(12) United States Patent
Boersma et al.

(10) Patent No.: US 11,812,846 B2
(45) Date of Patent: *Nov. 14, 2023

(54) HEATING AND COOLING SUPPLY FOR FACIAL BRUSH

(71) Applicant: KONINKLIJKE PHILIPS N.V., Eindhoven (NL)

(72) Inventors: Joldert Maria Boersma, Eindhoven (NL); David Alonso Canadas, Eindhoven (NL); Marc Leendert Verwillegen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/574,599

(22) Filed: Jan. 13, 2022

(65) Prior Publication Data

US 2022/0133026 A1    May 5, 2022

Related U.S. Application Data

(63) Continuation of application No. 15/767,166, filed as application No. PCT/EP2016/074427 on Oct. 12, 2016, now Pat. No. 11,259,627.

(30) Foreign Application Priority Data

Oct. 13, 2015  (EP) ..................... 15189473

(51) Int. Cl.
*A46B 15/00*  (2006.01)
*A46B 13/00*  (2006.01)
*A46B 13/02*  (2006.01)

(52) U.S. Cl.
CPC .......... *A46B 15/003* (2013.01); *A46B 13/008* (2013.01); *A46B 13/02* (2013.01); *A46B 2200/102* (2013.01)

(58) Field of Classification Search
CPC .......... A61H 7/00; A61H 7/002; A61H 7/004; A61H 7/005; A61H 2001/0153;
(Continued)

(56) References Cited

U.S. PATENT DOCUMENTS 4,860,748 A    8/1989  Chiurco
6,355,007 B1   3/2002  Zuckerbrod
(Continued)

FOREIGN PATENT DOCUMENTS

CN    203169845 U    9/2013
JP    2008093034 A    4/2008
(Continued)

*Primary Examiner* — Rachel T Sippel
*Assistant Examiner* — Jacqueline M Pinderski

(57) ABSTRACT

A skin treatment device especially for use for treating skin in terms of cleaning, exfoliating and/or massaging the skin. The device includes a housing and a skin treatment head releasably attached to the housing. The skin treatment head being rotatable around an axis element associated with the housing, wherein the housing encloses an actuator configured to rotate the skin treatment head, wherein the skin treatment head includes one or more brushes associated with a support element, wherein the device further includes a first thermally conductive element configured at a shortest distance to the one or more brushes selected from the range of 0-40 mm, and a thermoelectric element configured to heat in a first mode the first thermally conductive element to provide a hot surface.

20 Claims, 9 Drawing Sheets

(58) Field of Classification Search
CPC ........ A61H 2001/0157; A61H 2001/02; A61H 2001/0214; A61H 2001/0221; A61H 2001/0228; A61H 2001/0235; A61H 2001/0242; A61H 2001/025; A61H 2001/0257; A61H 2001/0264; A61H 2001/0271; A61H 2001/0278; A61H 2001/0285; A61H 2001/12; A61H 2001/1215; A46B 13/023; A46B 13/001; A46B 9/005; A46B 9/0028

See application file for complete search history.

(56) References Cited

U.S. PATENT DOCUMENTS

| | | |
|---|---|---|
| 6,401,289 B1 | 6/2002 | Herbert |
| 7,695,207 B1 * | 4/2010 | Laghi ................... A46B 11/001 |
| | | 401/2 |
| 8,157,753 B2 | 4/2012 | Nichols |
| 9,826,823 B1 | 11/2017 | Velazquez |
| 11,259,627 B2 * | 3/2022 | Boersma .............. A46B 13/008 |
| 2006/0058714 A1 | 3/2006 | Rhoades |
| 2007/0239142 A1 | 10/2007 | Altchuler |
| 2009/0012434 A1 * | 1/2009 | Anderson ............ A61H 9/0057 |
| | | 601/6 |
| 2009/0177125 A1 | 7/2009 | Pilcher |
| 2011/0040235 A1 | 2/2011 | Castel |
| 2013/0046212 A1 * | 2/2013 | Nichols .................... A61N 1/00 |
| | | 601/18 |
| 2014/0100487 A1 | 4/2014 | Altschuler |
| 2014/0219701 A1 * | 8/2014 | Eberlein .............. A45D 34/041 |
| | | 401/2 |
| 2015/0088050 A1 | 3/2015 | Chang |
| 2015/0121900 A1 * | 5/2015 | Yamazaki .............. A45D 34/04 |
| | | 62/3.3 |
| 2015/0313354 A1 | 11/2015 | Mongan |
| 2016/0324306 A1 | 11/2016 | Martin |

FOREIGN PATENT DOCUMENTS

| | | |
|---|---|---|
| KR | 20130062788 A2 | 6/2013 |
| KR | 101563327 B1 | 10/2015 |

* cited by examiner

HEATING AND COOLING SUPPLY FOR FACIAL BRUSH

CROSS REFERENCE TO RELATED APPLICATIONS

This application is a continuation of U.S. application Ser. No. 15/767,166, filed on Apr. 10, 2018, which is the U.S. National Phase application under 35 U.S.C. § 371 of International Application No. PCT/EP2016/074427, filed on Oct. 12, 2016, which claims the benefit of European Patent Application No. 15189473.0 filed on Oct. 13, 2015. These applications are hereby incorporated by reference herein.

FIELD OF THE INVENTION

The invention relates to a device for treating skin. The invention further relates to a housing and/or a skin treatment head for providing such device.

BACKGROUND OF THE INVENTION

Brushes for treating the skin are known in the art. US2006/0058714, for instance, describes an apparatus including a handle capable of manipulation by a human hand, and one or more head portions to mate to various types of treatment attachments, which may be moved over an area of skin and/or body part by a motion generator moving the head portions, and/or by a user manipulating the handle. Various suitable attachments include applicator attachments having abrasive surfaces, oxygenating attachments having pores through which oxygen may travel, brush attachments for cleaning and polishing, thermal attachments for heating and cooling, and light radiating attachments. The motion generator may move the attachments by vibrating, spinning, oscillating, or propagating sonic waves through the head portions. Thus, attachments may be attached and removed from the head portions to treating skin and/or body parts by abrasion, cleaning, polishing, lighting, or oxygenation. Moreover, during treatment an abrasive composition, a cleaning solution, and/or a polishing solution may be applied to the skin and/or body part.

U.S. Pat. No. 7,695,207B1 describes a shaving gel applicator including different embodiments that include an annular brush, a disc-shaped brush, a plurality of circumferentially spaced apart disc-shaped brushes, a pair of straight brushes, a single straight brush, and more. Some of the brushes are mounted for rotary motion and some for reciprocation in a linear motion. Heat is applied to the brushes to heat shaving gel deposited on the brushes. The shaving gel is dispensed from a cartridge that is releasably engaged to the applicator. A detector detects the type of cartridge in use and adjusts the amount of heat to be applied and the brush rotation or reciprocation speed that optimizes the performance of the shaving gel in that cartridge. In alternative embodiments, the gel is heated in a gel pack before it is dispensed onto the brushes.

CN203169845 describes a photonic beauty instrument and a charging seat thereof. The photonic beauty instrument comprises a housing and a functional head arranged on the upper end of the housing. A power source assembly and a PCB plate are arranged in the housing. The power source assembly is electrically connected with the PCB plate. An IPL assembly is arranged in the functional head, and is respectively electrically connected with the PCB plate and the power source assembly. With the photo-rejuvenation device, bio-stimulation photolysis heat are provided for human skins through intense pulsed lights generated by the IPL assembly, such that good wrinkle removing, spot removing, skin rejuvenation, skin tightening, and whitening effects are provided for skins. A charging circuit board is arranged in the charging seat. A cavity for accommodating the photo-rejuvenation device is provided on the charging seat. A charging contact corresponding to a charging contact plate is arranged in the cavity. A USB interface is arranged on one side of the charging seat. The USB interface, the charging circuit board, and the charging contact are sequentially electrically connected. The charging seat can charge the photo-rejuvenation device, and can assist the photo-rejuvenation device for carrying out sterilization and disinfection upon a brush.

US2009177125 describes an apparatus and corresponding method for treatment of skin conditions which includes a brush head member which comprises a first portion which includes a plurality of rings of bristle tufts, the first portion oscillating in operation through a selected angle at a selected frequency and a second portion which also includes a plurality of rings of bristle tufts concentric with the first portion, the second portion remaining stationary in operation. At least one monochromatic light source is included, providing light directed from the brush head in a direction substantially the same as the bristle tufts, such that the light impinges on the area of skin of the user acted on by the oscillating brush head.

SUMMARY OF THE INVENTION

Sebaceous glands are microscopic exocrine glands in the skin that secrete an oily or waxy matter, called sebum, to lubricate and waterproof the skin and hair of mammals. In humans, they are especially found on the face and scalp, and are also found on all parts of the skin except the palms of the hands and soles of the feet.

Consumer products aiming to remove sebum from the skin for cosmetic purposes or to target one or more of the causes of oily skin are based on mechanical or chemical functionality. These methods suffer from the fact that sebum is a substance of high viscosity and therefore of low mobility at standard conditions. This, combined with the fact that the human skin has upper limits for the amount of applied pressure or chemical concentrations, results in difficulty to effectively remove sebum while complying with other consumer requirements such as acceptable treatment times (about 2 minutes) and cordless devices.

Hence, it is an aspect of the invention to provide an alternative skin treatment device, which preferably further at least partly obviates one or more of above-described drawbacks, and which device may especially be used for treating skin in terms of cleaning, exfoliating and/or massaging the skin of a user, even more especially for removing sebum from the skin.

Sebum outflow is influenced by capillary forces between the outmost skin layer and the follicular reservoir. By partially emptying the follicular reservoir during skin cleansing the skin can remain substantially oil-free for a longer time compared to only surface cleaning.

In the invention, it is proposed to increase skin temperature above the sebum melting temperature of 32.9° C., leading to a higher sebum outflow, which increases the mobility and permeability of sebum during cleansing. In the invention, it is also proposed to optionally cool the skin after cleansing in order to coagulate temporally the sebum, leading to a combined effect on longer lasting oil free skin compared to manual cleaning. The invention relates to a mechanical stress and heat delivery system, where e.g., a liquid is used as a medium between device and the skin. The system may amongst others be intended for treatment of sebum and/or sebaceous follicle related skin issues such as for example seborrhea (oily skin) and acne vulgaris. The invention aims to increase the effectiveness of sebum removal and/or the effectiveness of cosmetic or therapeutic substances which can be contained in the liquid medium that is applied to the skin.

Hence, in a first aspect the invention provides a device ("skin treatment device") for treating skin comprising a housing and a skin treatment head (herein also indicated as "treatment head" or "head") rotatable associated with said housing, wherein the housing encloses an actuator configured to rotate said skin treatment head (relative to the housing), wherein the skin treatment head comprises one or more brushes associated with a support element (also comprised by the treatment head), wherein the device further comprises a first thermally conductive element, wherein especially the first thermally conductive element is configured at a shortest distance (d1) to the one or more brushes especially selected from the range of 0-40 mm, and wherein the device comprises a thermoelectric element (especially a "Peltier element") configured to heat in a first mode said first thermally conductive element.

With such device, the skin of a user can be subjected to one or more of cleaning, exfoliating and massaging, while due to the heating the sebum can better be removed. This may lead to a better skin treatment result. With the optional cooling, after the skin cleaning, exfoliating and/or massaging, the skin can further recover and relax due to contact with a cold part of the device. The cooling may also add to the time the skin is perceived less oily.

The device described herein is especially configured for one or more of cleaning, exfoliating and/or massaging the skin of a user. The device may especially be used in combination with a liquid. The liquid can be applied to the one or more brushes and/or to the skin. The liquid may especially be a cleansing liquid, such as including a soap. Optionally, the liquid may also comprise additives such as one or more of (a) a cosmetic or skin care material, and (b) a pharmaceutical material.

As indicated above, with the device the skin of a user can be subjected to one or more of cleaning, exfoliating and massaging. Especially, these actions will occur due to application of the rotating skin treatment head (with one or more brushes) on the skin, in combination with the liquid, and moving the treatment head over the skin. Hence, the invention also provides a method for treatment of a skin comprising applying the rotating skin treatment head to the skin, especially in combination with a liquid, and optionally moving the treatment head over the skin. The method may especially be a cosmetic method. Hence, treating the skin is especially done only for cosmetic purposes. Especially, the method may include heating, with the device, during application of the head to the skin. Further, the method may include, after application of the rotating treatment head to the skin, applying a cold surface of the device to the skin.

The device comprises essentially at least two parts, a housing and a skin treatment head. However, the device may comprise further parts, e.g., a safety or protection cap, an electrical wire, etc.

The housing includes an actuator, especially an electro motor, configured to rotate said skin treatment head. Further, the housing may especially include a rechargeable battery. Yet further, the housing may especially include a control system, configured to control the actuator and optionally also the thermoelectric element. Especially, the housing may thus enclose the actuator and e.g., a rechargeable battery, a control system, etc. Further, the housing may include customary elements like a user interface (functionally coupled with the control system), LED indicators, etc. Yet further, the housing may optionally also include a thermally conductive element that can be cooled (see further also below). Especially, the housing itself, or the outer part of the housing, may thus at least partially comprise one or more of the user interface, LED indicator(s), and the thermally conductive element that can be cooled.

The device may be configured to recharge the rechargeable battery (such as enclosed by the housing), for providing electrical power to at least the actuator, wired or wireless (like via induction). Hence, to this end the device may also comprise a receiver coil for wireless charging of the rechargeable battery.

The treatment head is rotatably associated with said housing. This especially implies that the treatment head is physically connected with the housing, but can rotate relatively to the housing. The actuator comprised by the housing rotates, during use of the device, the treatment head. In embodiments, the treatment head is associated to the housing in a fixed way, i.e., not intended to be removed during its lifetime. However, in other embodiments the treatment head may releasably be associated with the housing. This may e.g., be used to replace the treatment head with a new treatment head or another type of treatment head. For instance, different treatment heads may be used for different treatments, such as in terms of intensity and/or in terms of body parts, like softer brushes for treatment of the cheeks and harder brushes for treatment of the legs, etc. Optionally, a part of the treatment head may be releasably associated with the remainder of the treatment head (such as e.g., the part with the one or more brushes (see also below).

The skin treatment head especially comprises a plurality of bristles. Bristles are herein also indicated as filaments. Such bristle may especially be a single filament or such bristle may e.g., be based on a tuft, which tuft may provide two filaments extending from the support element. The filaments or bristles are generally configured in groups ("brushes"). Hence, the skin treatment head comprises especially a plurality of brushes. Sometimes, in the art the entire configuration of subsets of bristles is indicated as brush.

Hence, the skin treatment head comprises one or more brushes associated with a support element. The one or more brushes have a brush height relative to a support plane defined by the support element. The one or more brushes are especially 1-15 mm, such as about 1.5-10 mm long (calculated from the support) (i.e., height), and about 0.1-1 mm thick bristles, wire or other filaments, often of polymeric materials, such as a polyamide (like Nylon), a polyester, a polypropylene, a poly-olefine, and natural (animal) hairs. The one or more brushes, or bristles, are standing, but may be bended under influence of pressure, such as when moving the one or more brushes over the skin. The treatment head may include one or more brushes, such as at least 2 brushes, such as 5-100 brushes, though more may also be possible. Especially, the treatment head may include at least about 20 bristles (filaments), even more especially at least 50 bristles, such as in the range of 100-10,000, though more may also be possible. The bristles (filaments) may be anchored in the support, comprised by the treatment head. The bristles extend from the support. Hereby, the support defines a support plane from which the bristles extend. Hence, the one or more brushes (and thus bristles) have a brush height (h1) relative to a support plane (P) defined by the support element (especially heights of 1.5-10 mm; see also above). Note that not all brushes necessarily have the same height. The height may vary over the support. For instance, part of the bristles may be longer and others may be shorter. Even the bristles within a brush may have different heights.

The support may in embodiments be curved in one or two directions. In embodiments the support is flat and in other embodiments, the support may have the shape of a segment of a sphere. The area of the support (plane) may e.g., be in the range of about 1-15 cm$^2$, such as about 1.5-10 cm$^2$.

As indicated above, during the treatment of the skin with the treatment head (with the one or more brushes), the skin may also advantageously be heated (or optionally cooled). Hence, the device may further comprise a first thermally conductive element. The thermally conductive element may be heated directly (e.g., a metal body or non-metal body, like a ceramic, with one or more electrical wires within the body) or may be heated indirectly (e.g., a body that transfers heat to the first thermally conductive element). Especially, the (first) thermally conductive material may have a thermal conductivity of at least 5 W/(m K), such as at least 10 W/(m K), especially at least 100 W/(m K). Examples of suitable materials include steel, aluminum, copper, AlN, BN, SiC, etc. A part of the (first) thermally conductive element may be provided with a coating. Such coating may especially be applied at the part of the (first) thermally conductive element that is configured to be in contact with the skin. Such coating may be configured to improve gliding and/or to prevent migration of substances, such as from the cleansing liquid, into the (first) thermally conductive element.

Especially, the first thermally conductive element is configured such that when applying the skin treatment head to the skin, the first thermally conductive element can also be in physical contact with the skin. Hence, especially the first thermally conductive element may be comprised by the treatment head, or may be configured within part of the treatment head or is configured adjacent to the treatment head. As indicated above, especially the first thermally conductive element is configured at a shortest distance (d1) to the one or more brushes selected from the range of about 0-40 mm, even more especially selected from the range of about 0-20 mm, such as at least about 0.5 mm. This shortest distance may especially be defined as the shortest distance between a bristle (filament) closest to the first thermally conductive element.

In an embodiment, the first thermally conductive element has an element height (h2) higher than said support plane (P). Hence, relative to the support plane, also the first thermally conductive element (or at least part thereof) protrudes. Therefore, in embodiments the first thermally conductive element has an element height (h2) higher than said support plane (P). Further, especially the element height is equal to or lower than the brush height (h1), especially lower, such as in the range of 30-80% of the brush height.

In specific embodiments, the first thermally conductive element is configured adjacent to the skin treatment head. For instance, the first thermally conductive element may at least partially perimetrically surround the treatment head. In such embodiments, the first thermally conductive element may extend beyond the support plane, but may also optionally be at the same height or lower, however especially at least within about 0-40 mm, such as at least about 0.5 mm, from the bristle(s) configured closest to the first thermally conductive element.

Especially, the skin treatment head is configured to rotate about an axis element. In embodiments the first thermally conductive element is comprised by the axis element or the first thermally conductive element is associated with the axis element. For instance, the axis element may in embodiment be the first thermally conductive element, or the axis element may include an end comprising the first thermally conductive element. Especially, the first thermally conductive element is configured stationary.

For heating of the first thermally conductive element the device comprises a thermoelectric element. Hence, this thermoelectric element is configured to heat (in a first mode) said first thermally conductive element. The phrase "in a first mode" especially indicates that the device at least includes a single setting or mode, wherein the device heats the first thermally conductive element. The device, i.e., the thermoelectric element, may heat the first thermally conductive element especially while rotating the treatment head, and/or optionally while not rotating the treatment head. However, in embodiments the device may include further settings, such as related to one or more of the heating temperature, or even a mode wherein the first thermally conductive element is cooled. An advantage of using a thermoelectric element is that such heating device is more versatile than standard heating devices. With a thermoelectric element, one may—if desired—not only heat, but also cool. Hence, the device is especially configured to heat and/or cool with the thermoelectric element a thermally conductive element (respectively) or thermally conductive elements (at the same time (and/or sequentially)), see also below.

Especially, the thermoelectric element comprises a Peltier element comprising two different conductors or semiconductors. As indicated above, one or both of the semiconductors may also be in thermal contact with the first thermally conductive element or second thermally conductive element. A typical Peltier heat pump device involves multiple junctions in series, through which a current is driven. Some of the junctions lose heat due to the Peltier effect, while others gain heat. Thermoelectric heat pumps exploit this phenomenon, as do thermoelectric cooling devices found in refrigerators. Especially, the thermoelectric element includes two thermally conductive elements (herein also indicated as thermal conductors), such as ceramic plates, one used for cooling and the other used for heating (or vice versa). These thermally conductive elements of the thermoelectric element may be used as such, or may be in thermal contact with the first thermally conductive element and second thermally conductive element, respectively. The term "in thermal contact" implies an arrangement of components allowing transfer of heat or cold. Especially, the thermally conductive elements of the thermoelectric element may thus be used as such or may be in physical contact with the first thermally conductive element and second thermally conductive element, respectively.

As indicated above, the device is configured to heat in a first mode. The phrase "in a first mode" indicates that the device at least allows a single mode (during use of the device) such as "on". However, as described herein the device may also be configured to cool in a second mode. Further, the device may be configured to provide a plurality of (first) modes, such as different heating temperatures. Likewise, the device may also be configured to provide a plurality of (second) modes, such as different cooling temperatures. The first mode(s) may be associated with one or more rotational speeds of the treatment head. The second mode(s) may optionally also be associated with one or more rotational speeds of the treatment head.

The thermoelectric element may be configured at one side in thermal contact with a heat sink. Hence, the device may further comprise a heat sink. For instance, the thermally conductive element of the thermoelectric element not being used as or not in thermal contact with the first thermally conductive element may be in thermal contact, especially in physical contact, with a heat sink. Would in a second mode the first thermally conductive element be cooled, than heat can be dissipated from the other thermally conductive element of the thermoelectric element via the heat sink. In embodiments, the second thermally conductive element is configured as heat sink. Yet in further embodiments, the device housing may further include a (small) fan, configured to cool the heat sink and/or second thermally conductive element (during the second mode).

The (first) thermally conductive element may especially be heated to a temperature selected from the range of 25-50° C., especially 34-50° C. At such temperature, the sebum may become flowable enough to be at least partly removed from the skin. Hence, when heating a (first) thermally conductive element, heating may especially be done at a temperature selected from the range of 25-50° C., especially 34-50° C., such as 34-45° C., such as 34-43° C. Further, the (first) thermally conductive element may especially be cooled to a temperature selected from the range of 5-30° C., such as 5-25° C., such as 10-20° C. At such temperature, the just treated skin may benefit from the cooler element. Hence, when cooling a (first) thermally conductive element, cooling may especially be done at a temperature selected from the range of 5-30° C., such as 5-25° C., like 10-25°, such as 10-20° C. When heating the (first) thermally conductive element, the second thermally conductive element and/or heat sink may thus be cooled. Likewise, when cooling the (first) thermally conductive element, the second thermally conductive element and/or heat sink may thus be heated. Heating and or cooling may also include heating or cooling at different temperatures during the heating or cooling time, respectively. For instance, the term "heating" may also refer to a heating scheme with different temperatures (selected from the above mentioned ranges). Likewise, the term "cooling" may also refer to a cooling scheme with different temperatures (selected from the above mentioned ranges).

Optionally, the heating temperature may be controlled by a control system. Further, yet optionally heating and/or cooling may be controlled as function of a rotational speed of the treatment head.

Optionally, the heating and/or cooling by the thermoelectric element may be done in response to a temperature sensor signal of a sensor configured to sense the temperature of the (first) thermally conductive element.

A cooling can be done with the first thermally conductive element or with a second thermally conductive element. Both embodiments are described herein.

In specific embodiments, the thermoelectric element is configured to heat in a first mode said first thermally conductive element to a temperature, especially in the range of above 25° C., especially in the range of 34-45° C., and the thermoelectric element is (also) configured to cool in a second mode said first thermally conductive element to a temperature selected especially from the range of 10-25° C. The second mode may especially be the mode wherein the treatment head does not rotate. For instance, after treatment by application of the rotating treatment head to the skin (first mode), the same part of the skin may be cooled (second mode). However, optionally during part of the treatment of the skin with the (rotating) brush(es), also cooling may be applied. Hence, optionally also during the second mode the treatment head may rotate.

The thermoelectric element may especially include different electrically (semi)conductive elements between which a voltage difference is applied, by which the two different elements get different temperatures. This principle may be used for heating or for cooling. By changing polarity, the same (first) thermally conductive element may be heated or cooled. As indicated above, in embodiments one of the thermal conductive elements of the thermoelectric element may be in thermal contact with the (first) thermally conductive element; in other embodiments, one of the (electrical) conductive elements of the thermoelectric element is essentially the (first) thermally conductive element. Hence, the thermoelectric element may be used for heating or cooling the (first) thermally conductive element, but the thermoelectric element may also be used for heating the first thermally conductive element and for cooling a second thermally conductive element.

The terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The term "thermoelectric element" may also refer to a plurality of (different) thermoelectric elements, optionally stacked to provide a stacked thermoelectric element. A stacked thermoelectric element may be able to provide larger temperature differences.

The second thermally conductive element may be configured within the housing. In embodiments, the cold may (simply) be dissipated (e.g., with a heat sink). However, especially the cooling effect may also be used for e.g., cooling the skin.

Hence, in embodiments the housing comprises a second thermally conductive element, wherein the thermoelectric element is configured to cool in the first mode said second thermally conductive element, especially to a temperature selected from the range of 5-25° C. For instance, while treating the skin, the skin gets into contact with the treatment head and is heated by the first thermally conductive element. Thereafter, the skin may be contact with the second thermally conductive element, and can be cooled.

The second thermally conductive element is (actively) cooled (down) during the first mode. However, in embodiments also during the second mode, wherein the treatment head may be non-rotating, and wherein only a cooling action may be applied to the skin, the (second) thermally conductive element may be kept cool by the thermoelectric element. In such embodiments, especially the (second) thermally conductive element may be configured to be accessible to the skin, for cooling of the skin. Herein, several possible arrangements of the second thermally conductive element are described (see also below).

Optionally, the cooling by the thermoelectric element may be done in response to a temperature sensor signal of a sensor configured to sense the temperature of the (second) thermally conductive element. Of course, these embodiments may thus apply as well when the first thermally conductive element is used as cooling element (see also above).

The second thermally conductive element may be configured at different positions at the housing. The housing comprises a first end closest to the skin treatment head and a second end farthest away from the skin treatment head. In specific embodiments, the second thermally conductive element is configured between the first end and the second end. For instance, a part close to the treatment head may be used as cooling spot. After treatment of the skin, that part of the device may be contact with the (treated) skin. Alternatively or additionally, the second thermally conductive element is configured at the second end. In such embodiments, the device may be turned upside down after the brushing of the skin and be contacted with the cooling spot at the other side of the device.

In specific embodiments, the second thermally conductive element is just below the treatment head. When removing the (removable) treatment head (after treating the skin in the first mode), the skin may be contacted with the cooling spot provided by the second thermally conductive element that becomes accessible to the skin by the removal of the treatment head. Hence, in embodiments the second thermally conductive element is configured at the first end, wherein the skin treatment head is releasable associated with the housing such that when the skin treatment head is associated with the housing, the skin treatment head is configured to at least partially shield the second thermally conductive element. Hence, when the treatment head is removed, the second thermally conductive element is not shielded anymore and becomes accessible for application to the skin.

The second thermally conductive element may be configured at a second end, between the second end and the first end, and may thus also be configured at the first end. In yet other embodiments, the second thermally conductive element is comprised by the treatment head. Optionally, this cooling spot provided by the second thermally conductive element of the treatment head may be used for cooling the skin. This may e.g., be achieved when this second thermally conductive element is substantially not accessible to the skin in the first mode, but becomes accessible when the treatment head is removed from the housing. For instance, the second thermally conductive element may be configured at a side of the treatment head configured opposite of the one or more brushes and configured closest to the housing when the treatment head is associated with the housing. Hence, in embodiments the skin treatment head comprises a second thermally conductive element, wherein the thermoelectric element is configured to cool in the first mode said second thermally conductive element, and wherein the skin treatment head is releasable associated with the housing such that when the skin treatment head is associated with the housing, the housing is configured to at least partially shield the second thermally conductive element.

In yet further embodiments, the skin treatment head may be configured upside down, especially after removing the support with one or more brushes, into the housing. In this way, the cooling of the second thermally conductive element may be continued after associating the skin treatment head in an upside down position to the housing. Hence, the housing (and actuator) may be configured to receive the skin treatment head and (functionally) associate therewith rotatably and in yet other embodiments, the housing (and actuator) may be configured to receive the skin treatment head in an upside down position and (functionally) associate for further cooling of the second thermally conductive element.

The second thermally conductive element may comprise the same material or same type of material as mentioned above especially in relation to the first thermally conductive element. Hence, above the characteristics in relation to the first thermally conductive element are often describe more general by using the phrase "(first) thermally conductive element". Further, at least part of the second thermally conductive element may also be provided with a coating. Such coating may especially be applied at the part of the (second) thermally conductive element that is configured to be in contact with the skin. Such coating may be configured to improve gliding and/or to prevent migration of substances, such as from the cleansing liquid, into the (second) thermally conductive element, or for other purposes.

Optionally, powering of the thermoelectric element may be configured such that the thermoelectric element is substantially independent of the source of power used for the actuator. In embodiments, the skin treatment head comprises a (rechargeable) battery configured to provide electrical power to the thermoelectric element (comprised by the treatment head). Here, the phrase "substantially independent of the source of power used for the actuator" does not exclude that the battery comprised by the treatment head is a rechargeable battery that can recharge via substantially the same mechanism as recharging a rechargeable battery for powering the actuator. The treatment head may also comprise a receiver coil for wireless charging of the rechargeable battery within the treatment head. However, also sliding contacts for providing power to the thermoelectric element may be applied.

When the treatment head comprises the first thermally conductive element or the second thermally conductive element, especially first thermally conductive element or the second thermally conductive element are releasable associated with the treatment head. In this way, these may be reused when the one or more brushes have to be replaced. Hence, in embodiments the skin treatment head is configured to rotate about an axis element, wherein the first thermally conductive element is releasable associated with the axis element, wherein especially (a) the first thermally conductive element is associated with the skin treatment head, and the second thermally conductive element is releasably associated with the skin treatment head, or (b) the second thermally conductive element and the first thermally conductive element are releasably associated with the skin treatment head. In an alternative configuration, the treatment head comprises the support element with one or more brushes, wherein the support element (with one or more brushes) is releasably associated with the (remainder of the) treatment head. Hence, when other brushes are desired, only the support element (with one or more brushes) may have to be replaced. Therefore, in yet a further aspect the invention also provides a support element with one or more brushes, wherein such support element is configured to be used for a treatment head with which it can be releasably associated, and which is especially configured to be used for the device as described herein.

The invention also provides the housing per se as described herein per se. Such housing may especially comprise one or both first and second thermally conductive elements. Further, such housing especially comprises the thermoelectric element. Hence, in yet a further aspect the invention also provides a housing (for use together with a skin treatment head rotatable associable with said housing), wherein the housing encloses an actuator (configured to rotate said skin treatment head, wherein the skin treatment head comprises one or more brushes associated with a support element, wherein the one or more brushes have a brush height (h1) relative to a support plane (P) defined by the support element), wherein (a) the housing comprises a first thermally conductive element (and the skin treatment head comprises a second thermally conductive element), or (b) wherein the housing comprises a first thermally conductive element and a second thermally conductive element, wherein the housing further comprise a source of electrical power, and wherein the first thermally conductive element and the second thermally conductive element are configurable in thermal contact with a thermoelectric element (i.e., with the respective thermal conductors comprised by the thermoelectric element). The source of electrical power is especially configured to provide electrical power to the actuator and optionally also the thermoelectric element.

The invention also provides the skin treatment head as described herein per se. Such treatment head may especially include a first thermally conductive element and optionally also a second thermally conductive element. Hence, optionally the skin treatment head may include the thermoelectric element, and in yet further embodiments even a rechargeable battery. Hence, in embodiments the invention also provides a skin treatment head (for use together with a housing and rotatable associable therewith, wherein the housing encloses an actuator configured to rotate said skin treatment head), wherein the skin treatment head comprises one or more brushes associated with a support element, wherein the one or more brushes have a brush height (h1) relative to a support plane (P) defined by the support element, wherein (a) the skin treatment head comprises a first thermally conductive element (and the housing comprises a second thermally conductive element), or (b) wherein the skin treatment head comprises a first thermally conductive element and a second thermally conductive element, wherein (one or more of the housing and) the skin treatment head further comprise a source of electrical power, and wherein the first thermally conductive element and the second thermally conductive element are or configurable in thermal contact with a thermoelectric element (i.e., with the respective thermal conductors comprised by the thermoelectric element). The source of electrical power is especially configured to provide electrical power to the actuator and optionally also the thermoelectric element.

Yet further, the invention also provides a kit of parts comprising the housing and one or more treatment heads. Yet further, the invention also provides a kit of parts comprising the housing, the treatment head and one or more supports with one or more brushes, wherein especially the treatment head is configured to releasably associate the (respective) support(s) with one or more brushes. Yet, further, the invention also provides a kit of parts comprising a treatment head and one or more supports with one or more brushes, wherein especially the treatment head is configured to releasably associated the (respective) support(s) with one or more brushes.

Hence, in embodiments the thermoelectric element is configured to heat in a first mode said first thermally conductive element.

In yet further embodiments the thermoelectric element may be configured to cool in a first mode said first thermally conductive element.

In yet further embodiments the thermoelectric element may be configured to heat in a first mode said first thermally conductive element and cool in a second mode said first thermally conductive element.

In yet further embodiments, the device comprises a second thermally conductive element. This second thermally conductive element can be accessible to the user of the device without an additional measure or may be accessible to the user of the device with an additional measure, such as removal of the skin treatment head or arranging the skin treatment head upside down to the housing.

In (such further) embodiments, the thermoelectric element is configured to cool in a first mode said second thermally conductive element, especially when the thermoelectric element is configured to heat in a first mode said first thermally conductive element.

In (such further) embodiments, the thermoelectric element is configured to heat in a first mode said second thermally conductive element, especially when the thermoelectric element is configured to cool in a first mode said first thermally conductive element.

The device is especially a handheld device. Hence, the device may be designed to be used while being held in a single hand. Hence, the weight of the device is especially equal to or less than 1.75 kg, such as equal to or less than 1 kg, like in the range of 200-700 gram.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 3d-1 and 3d-2 illustrate cross-sectional views of different embodiments of the thermoelectric elements and the thermally conductive elements;

The schematic drawings are not necessarily on scale.

DETAILED DESCRIPTION OF THE EMBODIMENTS

Figure 1:
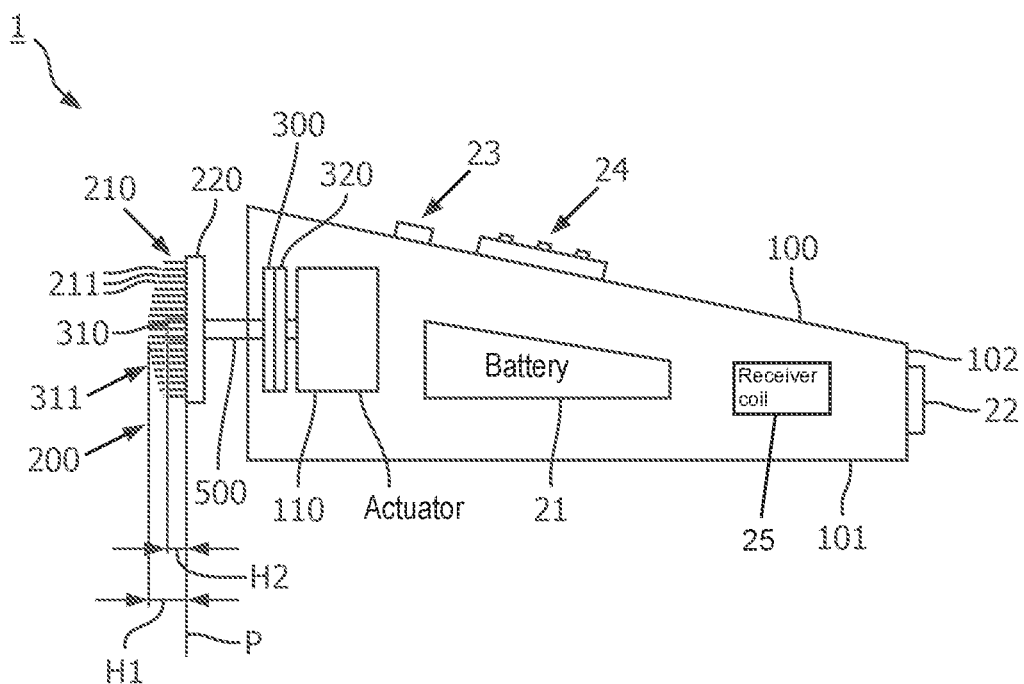
FIG. 1 schematically depicts an embodiment of the device.

FIG. 1 schematically depicts an embodiment of the device, indicated with reference 1, especially for use in exfoliating and/or removal of sebum from the skin. Here, the device, especially for treating the skin, comprises a housing 100 and a skin treatment head 200 rotatably associated with said housing 100. The housing 100 encloses an actuator 110 configured to rotate said skin treatment head 200. Further, the housings includes in this embodiment a rechargeable battery 21. Yet further, the housing 100 may comprise one or more LED indicators 23 and a user interface 24. Further, the housing may include a means 22 for receiving electrical power for charging the battery, such as a socket known in the art. The housing 100 comprises a first end 101 closest to the skin treatment head 200 and a second end 102 farthest away from the skin treatment head 200.

The skin treatment head 200 comprises one or more brushes 210 associated with a support element 220, wherein the one or more brushes 210, with bristles 211, have a brush height h1 relative to a support plane P defined by the support element 220. Note that in this schematic embodiment by way of example the bristles 211 have different heights.

Further, the device 1 further comprises a first thermally conductive element 310, in this embodiment having an element height h2 higher than said support plane P. The device 1 also comprises a thermoelectric element 300 configured to heat in a first mode said first thermally conductive element 310. Further, this thermoelectric element 300 may cool a second thermally conductive element 320. The rechargeable battery 21 may provide electrical power to the thermoelectric element 300. The thermoelectric element 300 may especially comprise a Peltier element, having two (semi)conductors of different materials. These (semi)conductors are in contact with a thermally conductive material, often ceramics, respectively, and may be the first and second thermally conductive element 310,320, respectively, or may be thermally coupled therewith. The surface or spot of the first thermally conductive element 310 that may be heated is indicated with reference 311. The device comprises an axis element 500, about which the treatment head rotates, and which in embodiment may comprise or be configured as first thermally conductive element 310. Especially, the (first) thermally conductive element 310 may have a thermal conductivity of at least 5 W/(m K), such as at least 10 W/(m K), especially at least 100 W/(m K). Examples of suitable materials include steel, aluminum, copper, AlN, BN, SiC, etc.

Figure 2A:
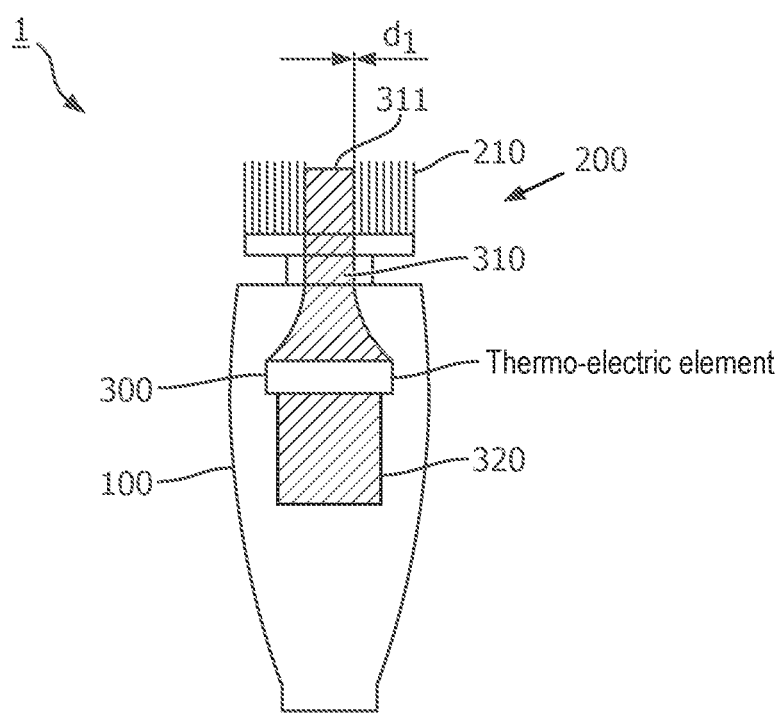
FIG. 2a illustrates an embodiment in which the skin treatment head is configured to rotate about an axis element wherein the first thermally conductive element is comprised by the axis element.

FIGS. 2a-2d schematically depict embodiments wherein the skin treatment head 200 is configured to rotate about an axis element 500 wherein the first thermally conductive element 310 is comprised by the axis element 500 or wherein the first thermally conductive element 310 is associated with the axis element 500. As can be seen, the element height h2 is equal to or lower than the brush height h1. On top of the first thermally conductive element 310 a coating may optionally be applied, to provide a softer feeling. This coating should especially be thin, or relatively highly thermally conductive. FIG. 2a schematically shows an embodiment wherein a second thermally conductive element is contained within the housing 100 and has no function in relation to skin treatment. In such embodiment, the second thermally conductive element may be configured as heat sink. Note that with reversing polarity, the first thermally conductive element can be cooled.

Hence, FIG. 2a shows an embodiment of the device 1 for treating skin comprising housing 100 and a skin treatment head 200 rotatably (around an axis element 500) associated with said housing 100, wherein the housing 100 encloses an actuator configured to rotate said skin treatment head 200, wherein the skin treatment head 200 comprises one or more brushes 210 associated with a support element 220, wherein the device 1 further comprises a first thermally conductive element 310, wherein the first thermally conductive element 310 is configured at a shortest distance d1 to the one or more brushes 210 selected from the range of 0-40 mm, and wherein the device 1 comprises a thermoelectric element 300 configured to heat in a first mode said first thermally conductive element 310 to provide a hot surface 311.

Figure 2B:
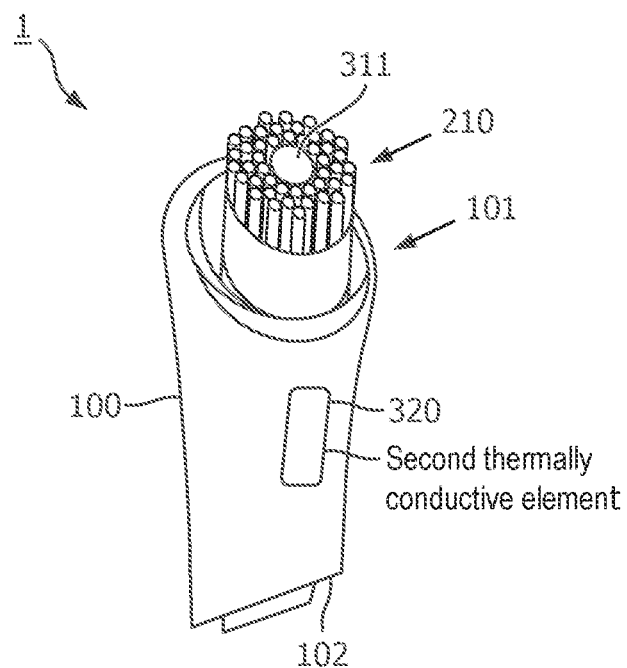
FIG. 2b illustrates an embodiment in which the second thermally conductive element is accessible to a user.
Figure 2C:
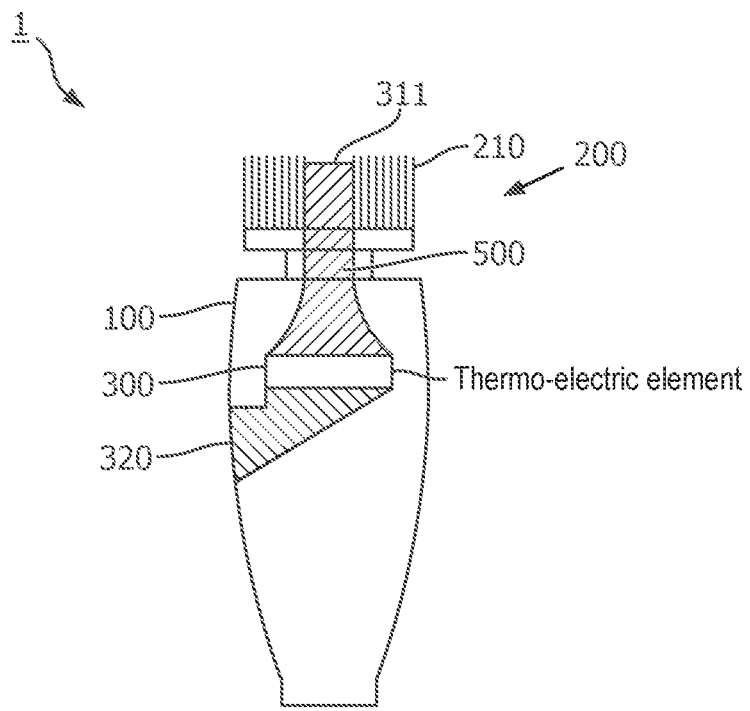
FIGS. 2c-2d illustrate cross-sectional views of embodiments in which the second thermally conductive element is accessible to a user.
Figure 2D:
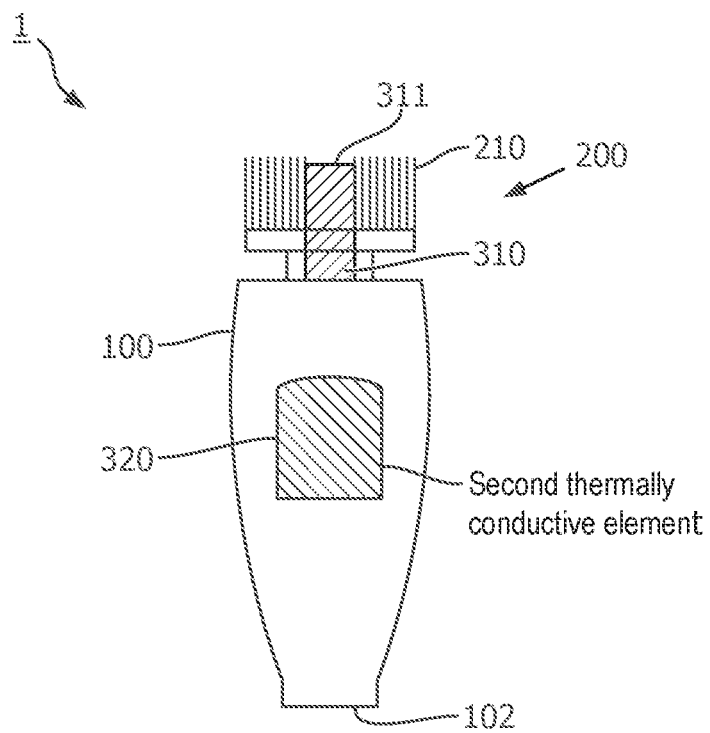

FIGS. 2b-2d schematically depict embodiments with a second thermally conductive element 320, accessible to a user, wherein the thermoelectric element 300 is configured to cool (in the first mode) said second thermally conductive element 320, such as to a temperature selected from the range of 5-25° C. In FIG. 2b, the second thermally conductive element 320 is configured between the first end 101 and the second end 102. In FIGS. 2c and 2d (which can be a cross-section and side view of the same embodiment) the second thermally conductive element 320 is configured between the first end 101 and the second end 102. After treatment with the treatment head, the cool second thermally conductive element 320 can be contacted with the skin. In such embodiment, the second thermally conductive element 320 may be configured as heat sink.

Figure 2E:
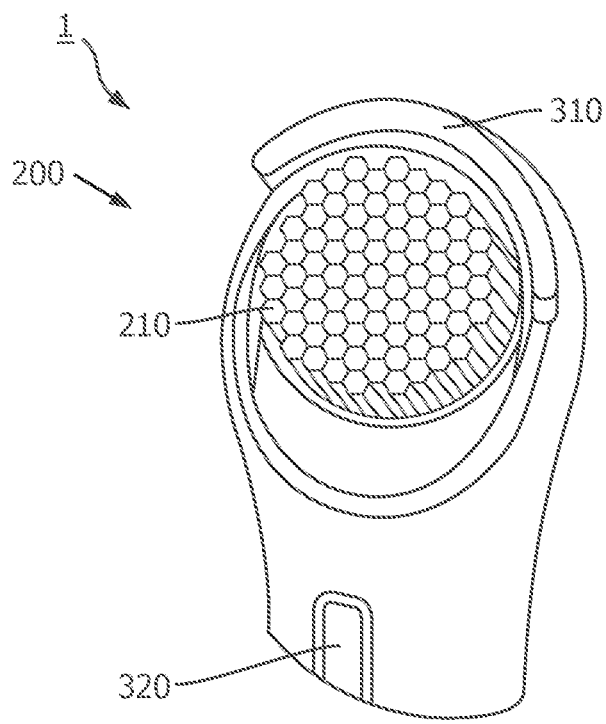
FIG. 2e illustrates an embodiment in which the second thermally conductive element is accessible to a user.

FIG. 2e schematically depicts an embodiment wherein the first thermally conductive element 310 is configured adjacent to the treatment head 200. The first thermally conductive element 310 may at least partly circumferentially surround the treatment head 200. Further, the second thermally conductive element 320 is configured at the second end 102.

Figure 2F:
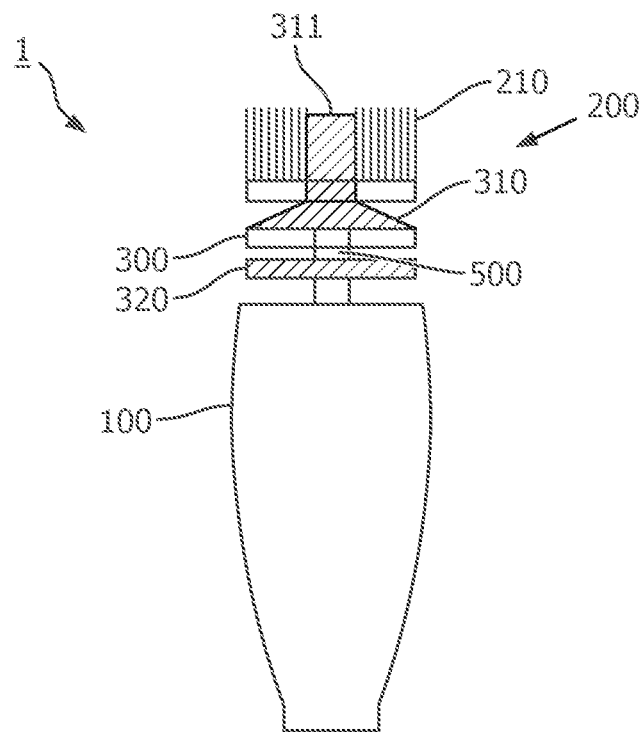
FIG. 2f illustrates a cross-sectional view of an embodiment in which the treatment head comprises a first thermally conductive element, a second thermally conductive element and a thermoelectric element.

FIG. 2f schematically depicts an embodiment wherein the first thermally conductive element 310 is comprised by the treatment head 200. The skin treatment head 200 comprises a second thermally conductive element 320. Also the thermoelectric element 300 may be comprised by the treatment head. Electrical powering may be done by a battery in the treatment head (see below) or by e.g., electrical slide contacts. Alternatively or additionally, electrical powering may be done via inductive powering. The thermoelectric element 300 may be configured to cool in the first mode said second thermally conductive element 320. The skin treatment head 200 is especially releasably associated with the housing 100 such that when the skin treatment head 200 is associated with the housing, the housing 100 is configured to at least partially shield the second thermally conductive element 320. By taking off the treatment head 200, the cold side, i.e., the second thermally conductive element 320 can be contacted with the skin to cool the skin.

Figure 2G:
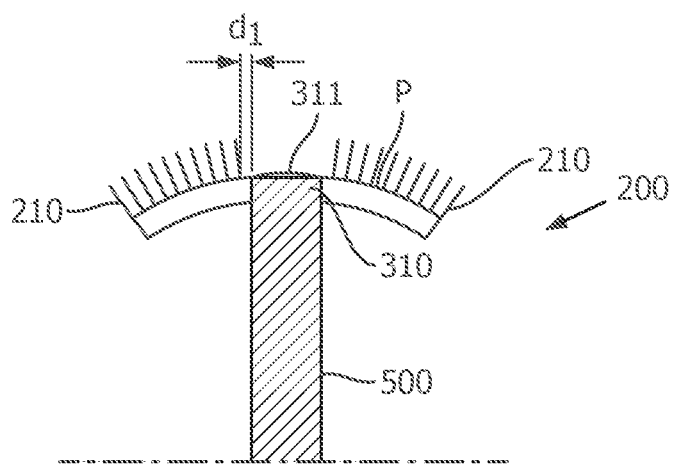
FIGS. 2g-i illustrate some embodiments of the first thermally conductive element.
Figure 2H:
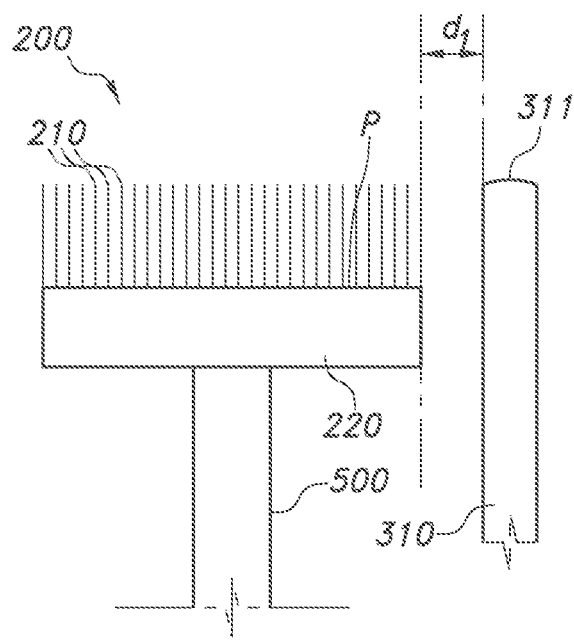
Figure 2I:
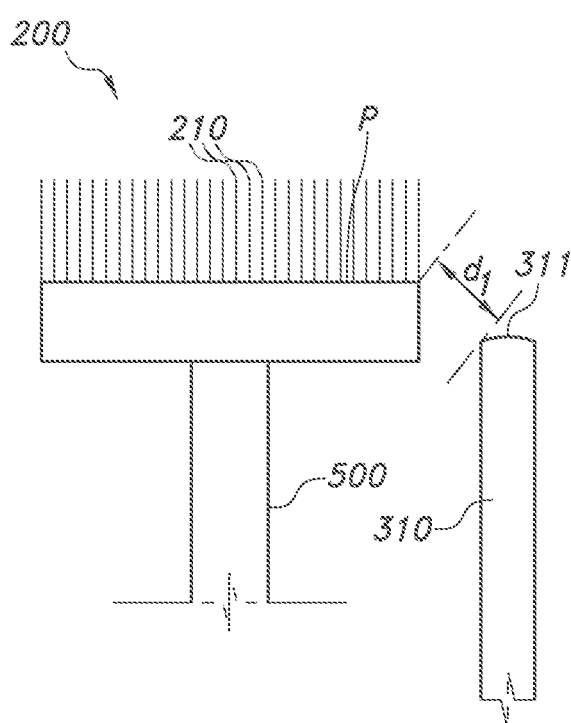

FIGS. 2g-2i schematically depict some configurations of the first thermally conductive element. In FIG. 2g the thermally conductive element is configured substantially at the same height as the support plane P. Here, the thermally conductive element 310 is comprised by the treatment head 200. Distance d1 indicates the shortest distance between the first thermally conductive element 310 and the brush(es) 210, i.e., a bristle configured closest to the first thermally conductive element 310. In FIG. 2h the thermally conductive element is configured substantially at the same height as the brush(es). Here, the thermally conductive element 310 is not comprised by the treatment head 200 but configured adjacent to the treatment head. The first thermally conductive element can also be configured lower than the brushes 210, or even lower than the support. An example of a configuration different from the schematically depicted configuration of FIG. 2h is schematically depicted in FIG. 2i.

Figure 3A:
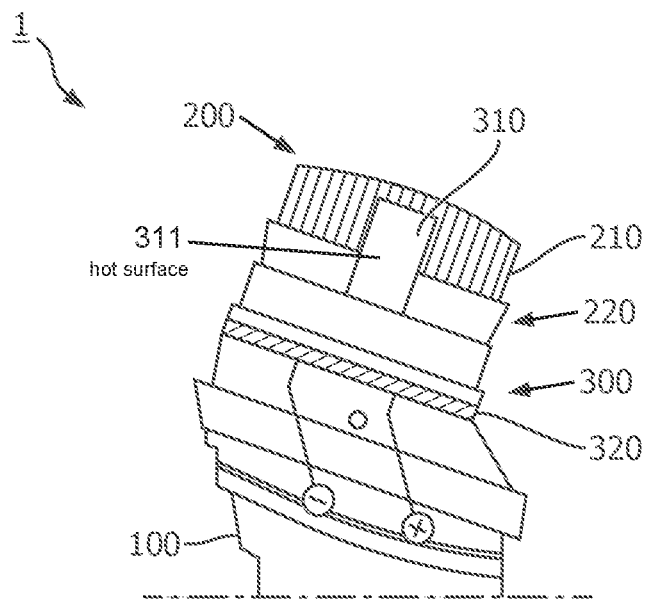
FIG. 3a illustrates an embodiment in which the treatment head is partially releasable.

FIG. 3a schematically depicts in more detail the embodiment also described in relation to FIG. 2f. However, it might also be possible to disconnect part of the treatment head 200, i.e., removing a releasable first thermally conductive element 310 and a releasable support element 220, by which the second thermally conductive element 320 becomes accessible to the user for cooling the skin.

Figure 3B:
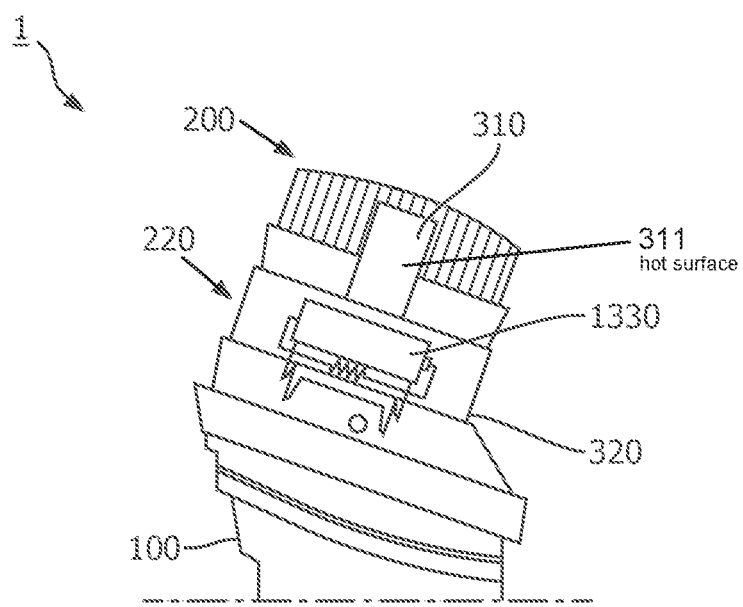
FIG. 3b illustrates an embodiment in which a rechargeable battery is configured within the treatment head for powering the thermoelectric element.

FIG. 3b schematically depicts an embodiment wherein a (rechargeable) battery 1330 is configured within the treatment head for powering the thermoelectric element 300.

Figure 3C:
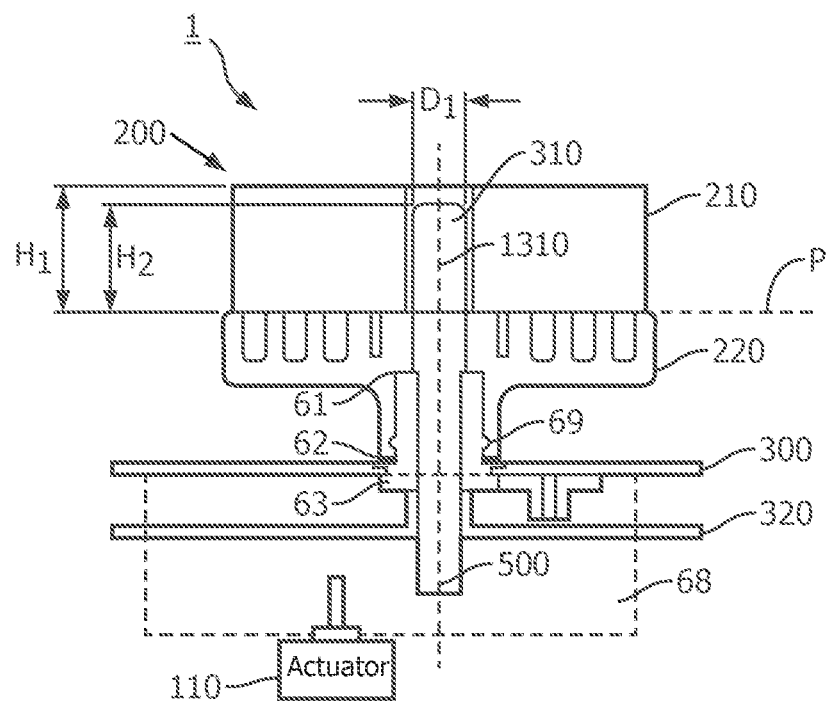
FIG. 3c illustrates an embodiment a portion of the device of FIG. 1 illustrating certain mechanical components including one or more seal interfaces, one or more gears, and a brush-click element.

FIG. 3c schematically depicts an embodiment of a part of the device 1. Reference 61 indicates a seal interface and reference 62 indicates a seal interface. Reference 63 indicates a gear (more gears may be available). Further, reference 68 indicates a gear box. Reference d1 is the diameter of the thermally conductive element 310. Reference 69 indicates a brush-click on element.

Figures 1, 2, 3D:
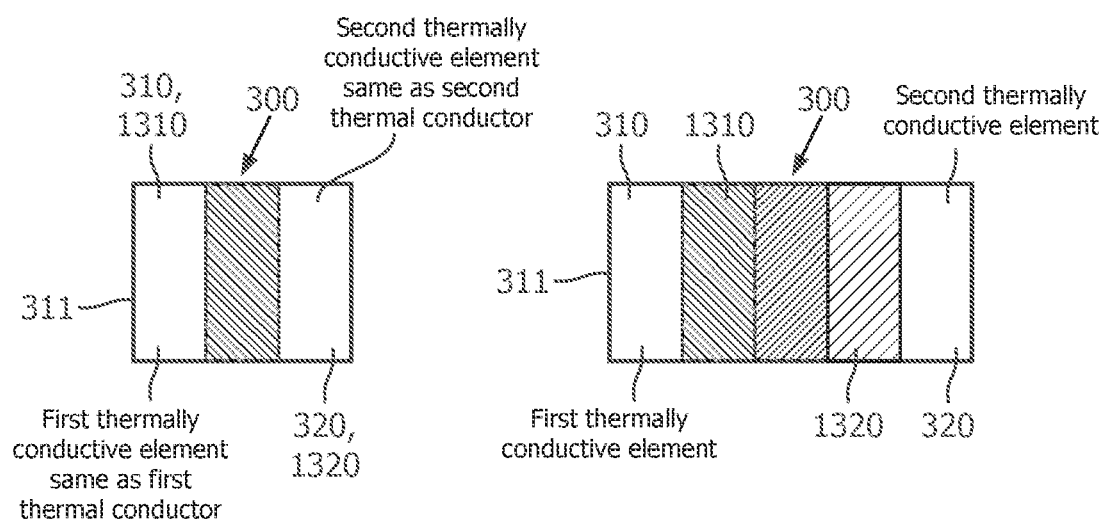

FIG. 3d schematically depicts two embodiments of the configuration thermoelectric element 300 and thermally conductive elements 310, 320. The thermoelectric element 300 comprises a "hot side" (hot side ceramic) and a "cold side" (cold side ceramic), indicated with references 1310 and 1320, respectively, which are herein indicated as the thermal conductors of the thermoelectric element 300. These may be configured as first and second thermally conductors 310, 320, respectively. Note that in such embodiments the shapes of one or more of the first and second thermally conductors may be different. Hence, in the left embodiment, in FIG. 3d-1, the thermal conductors 1310, 1320 of thermoelectric element 300 are (configured as) the first thermally conductive element 310 and second thermally conductive element 320, respectively. In the right embodiment, the thermal conductors 1310,1320 of the thermoelectric element 300 are in thermal contact with the first thermally conductive element 310 and second thermally conductive element 320 (here in physical contact).

Figure 3E:
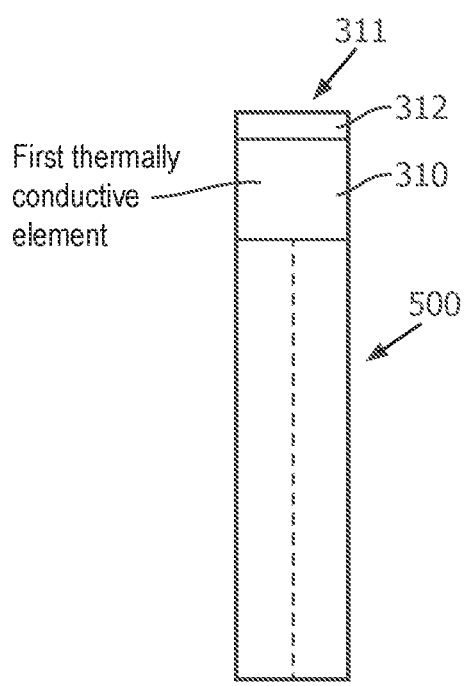
FIG. 3e illustrates an embodiment in which a coating is applied to the thermally conductive element used for heating.

FIG. 3e schematically depicts an embodiment wherein a coating 312 is applied to the thermally conductive element that is used for heating. This may provide a more flexible and/or softer surface.

Figure 3F:
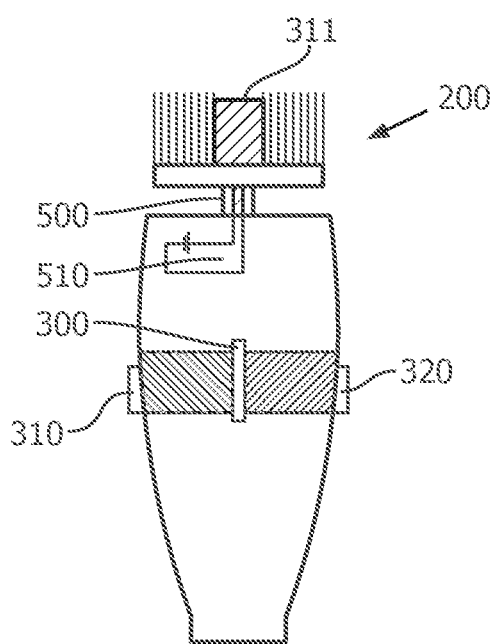
FIG. 3f illustrates a cross-sectional view of an embodiment in which an optional separate power source heats the thermally conductive element at the brush to provide a hot surface.
Figure 4:
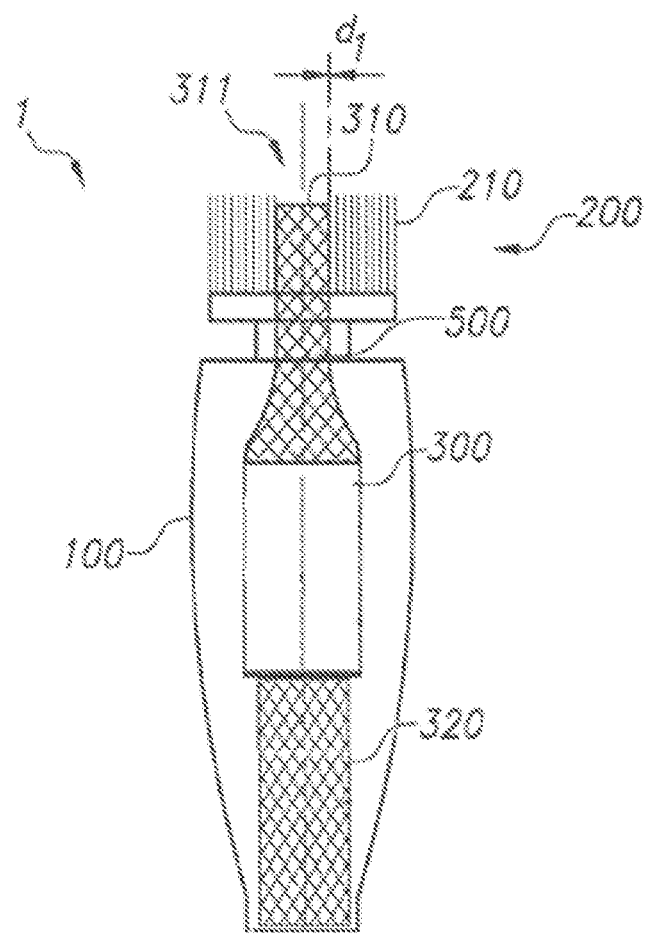

FIG. 3f schematically depicts another configuration wherein an optional separate power source 510 heats the thermally conductive element at the brush, to provide a hot surface 311, and wherein the thermoelectric element 300 is configured in the handle. Now, the handle comprises a first thermally conductive element 310, e.g., for heating the skin when desired, and a second thermally conductive element, e.g., for cooling the skin. With the relative simple construction of a resistance heating, also a hot surface may be provided at the head, either comprised by the head, as schematically depicted in FIG. 3f, or adjacent to the head (see e.g., FIGS. 2e, 2h and 2i). An example of a suitable material for resistance heating is a PTC material that changes electrical resistance as temperature increases. This may also make the heating intrinsically safe. Control of the temperature of the thermally conductive element that is heated may be done via a control unit, optionally together with a temperature sensor. Alternatively or additionally, temperature control may be done by using materials that may intrinsically reduce current, block current, or open current circuits, such as e.g., a positive temperature coefficient (PTC) material. Also materials may be used that with increasing temperature may be configured to decouple elements (open current circuits), such a bimetals, or other materials such as nitinol, etc. Other options may include e.g., a smart NFC tag with temperature sensor.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A device for treating skin, the device comprising:
   a housing having a first end and a second end;
   a skin treatment head coupled to the housing proximal to the first end, wherein the skin treatment head is rotatable relative to the housing;
   wherein
   the housing encloses an actuator configured to rotate the skin treatment head,
   the skin treatment head comprises one or more brushes attached to a support element;
   a first thermally conductive element arranged within the skin treatment head and positioned at a distance to the one or more brushes, wherein the distance is selected from a range of 0-40 mm,
   a second thermally conductive element arranged either (a) at a midpoint between the first end and the second end of the housing or (b) at the second end of the housing furthest away from the skin treatment head; and
   a thermoelectric element, wherein in a first mode, the thermoelectric element is configured to heat the first thermally conductive element and to cool the second thermally conductive element.

2. The device according to claim 1, wherein:
the one or more brushes have a brush height relative to a support plane defined by the support element,
the first thermally conductive element has an element height higher than the support plane,
the element height is equal to or lower than the brush height,
the first thermally conductive element is configured such that when applying the skin treatment head to the skin, the first thermally conductive element is in physical contact with the skin, and
the first thermally conductive element is stationary.

3. The device according to claim 1, wherein:
in the first mode, the thermoelectric element is configured to heat the first thermally conductive element to a temperature selected from a range of 34-45° C., and
in a second mode, the thermoelectric element is configured to cool the first thermally conductive element to a temperature selected from a range of 5-25° C.

4. The device according to claim 1, wherein the distance is selected from a range of 0.5-15 mm.

5. The device according to claim 1, wherein in the first mode, the thermoelectric element is configured to cool the second thermally conductive element to a temperature selected from a range of 5-25° C.

6. The device according to claim 1, wherein the second thermally conductive element is positioned at the second end of the housing furthest away from the skin treatment head at an outer surface of the housing.

7. The device according to claim 1, wherein the skin treatment head is releasably coupled to the housing such that when the skin treatment head is coupled to the housing, the skin treatment head is configured to at least partially shield the second thermally conductive element.

8. The device according to claim 1, wherein the skin treatment head is releasably coupled to the housing such that when the skin treatment head is coupled to the housing, the housing is configured to at least partially shield the second thermally conductive element.

9. The device according to claim 1, wherein the skin treatment head comprises a battery configured to provide electrical power to the thermoelectric element.

10. The device according to claim 1, wherein the skin treatment head is configured to rotate about an axis element wherein the first thermally conductive element is comprised by the axis element or wherein the first thermally conductive element is associated with the axis element.

11. The device according to claim 1, wherein the skin treatment head is configured to rotate about an axis element and the first thermally conductive element is releasably associated with the axis element, wherein (a) the first thermally conductive element is associated with the skin treatment head and the second thermally conductive element is releasably associated with the skin treatment head, or (b) the second thermally conductive element and the first thermally conductive element are releasably associated with the skin treatment head.

12. The device according to claim 1, wherein the thermoelectric element comprises a Peltier element comprising two different thermal conductors, wherein a first thermal conductor comprises the first thermally conductive element and wherein a second thermal conductor comprises the second thermally conductive element.

13. The device according to claim 1, wherein the first and second thermally conductive elements are each provided with a coating at a part of the element that contacts the skin of a user.

14. The device according to claim 1, wherein the first thermally conductive element at least partly circumferentially surrounds the treatment head.

15. The device according to claim 1, wherein the housing further comprises a control system configured to control the actuator and the first thermally conductive element, a user interface functionally coupled to the control system and at least one LED indicator.

16. The device according to claim 1, wherein the thermoelectric element is used for heating or cooling the first thermally conductive element while rotating the treatment head.

17. The device according to claim 1, wherein the thermoelectric element is used for heating or cooling the first thermally conductive element while not rotating the treatment head.

18. The device according to claim 1, wherein the treatment head comprises a receiver coil for wireless charging of a rechargeable battery.

19. The device according to claim 1, wherein
in the first mode, the thermoelectric element is configured to heat the first thermally conductive element at any one of a plurality of user selectable heating temperatures, and
in a second mode, the thermoelectric element is configured to cool the first thermally conductive element at any one of a plurality of user selectable cooling temperatures.

20. The device according to claim 1, wherein a heating temperature is controlled as a function of a rotational speed of the treatment head.

* * * * *